(12) United States Patent
Morton

(10) Patent No.: US 8,831,176 B2
(45) Date of Patent: Sep. 9, 2014

(54) HIGH ENERGY X-RAY INSPECTION SYSTEM USING A FAN-SHAPED BEAM AND COLLIMATED BACKSCATTER DETECTORS

(75) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 588 days.

(21) Appl. No.: 12/993,831

(22) PCT Filed: May 20, 2009

(86) PCT No.: PCT/GB2009/001275
§ 371 (c)(1),
(2), (4) Date: Feb. 22, 2011

(87) PCT Pub. No.: WO2009/141613
PCT Pub. Date: Nov. 26, 2009

(65) Prior Publication Data
US 2011/0135060 A1   Jun. 9, 2011

(30) Foreign Application Priority Data
May 20, 2008   (GB) .................................. 0809107.6

(51) Int. Cl.
*G01N 23/203* (2006.01)
*G01V 5/00* (2006.01)

(52) U.S. Cl.
CPC ............ *G01V 5/0016* (2013.01); *G01V 5/0025* (2013.01); *G01N 23/203* (2013.01)
USPC .............................................. 378/86; 378/57

(58) Field of Classification Search
CPC . G01N 23/203; G01N 23/201; G01V 5/0016; G01V 5/0025
USPC ................................ 378/57, 86, 87, 88, 89, 90
See application file for complete search history.

(56) References Cited

U.S. PATENT DOCUMENTS 2,831,123 A    4/1958  Daly
3,766,387 A   10/1973  Heffan et al.
(Continued)

FOREIGN PATENT DOCUMENTS

EP   0287707     11/1982
EP   00077018    4/1983
(Continued)

OTHER PUBLICATIONS

International Search Report PCT/GB2009/000515, Feb. 23, 2010, Rapiscan Security Products, Inc.

(Continued)

*Primary Examiner* — Glen Kao
(74) *Attorney, Agent, or Firm* — Novel IP

(57) ABSTRACT

This invention provides a scanning system for scanning an object in a scanning zone. The scanning system includes both a radiation source arranged to irradiate the object with radiation having a peak energy of at least 900 keV and a scatter detector arranged to detect radiation scattered from the object wherein the radiation source is arranged to irradiate the object over a plurality of regions to be scanned within a single irradiation event. The scatter detector includes a plurality of detection elements, each detection element being arranged to detect scattered radiation from a predefined part of the scanning zone and a signal processor arranged to calculate scatter intensity across the plurality of detector elements.

19 Claims, 4 Drawing Sheets

(56) References Cited

U.S. PATENT DOCUMENTS

| | | | |
|---|---|---|---|
| 3,770,955 A | 11/1973 | Tomita et al. | |
| 3,784,837 A | 1/1974 | Holmstrom | |
| RE28,544 E | 9/1975 | Stein et al. | |
| 3,904,923 A | 9/1975 | Schwartz | |
| 4,047,035 A | 9/1977 | Dennhoven et al. | |
| 4,139,771 A | 2/1979 | Dennhoven et al. | |
| 4,210,811 A | 7/1980 | Dennhoven et al. | |
| 4,216,499 A | 8/1980 | Kunze et al. | |
| 4,366,382 A | 12/1982 | Kotowski | |
| 4,430,568 A | 2/1984 | Yoshida et al. | |
| 4,566,113 A | 1/1986 | Donges et al. | |
| 4,599,740 A | 7/1986 | Cable | |
| 4,626,688 A | 12/1986 | Barnes | |
| 4,641,330 A | 2/1987 | Herwig et al. | |
| 4,709,382 A | 11/1987 | Sones | |
| 4,736,401 A | 4/1988 | Donges et al. | |
| 4,788,704 A | 11/1988 | Donges et al. | |
| 4,817,123 A | 3/1989 | Sones et al. | |
| 4,825,454 A | 4/1989 | Annis et al. | |
| 4,872,188 A | 10/1989 | Lauro et al. | |
| 4,884,289 A | 11/1989 | Glockmann et al. | |
| 4,979,202 A | 12/1990 | Siczek et al. | |
| 4,991,189 A | 2/1991 | Boomgaarden et al. | |
| 5,022,062 A | 6/1991 | Annis | |
| 5,065,418 A | 11/1991 | Bermbach et al. | |
| 5,091,924 A | 2/1992 | Bermbach et al. | |
| 5,098,640 A | 3/1992 | Gozani et al. | |
| 5,179,581 A | 1/1993 | Annis | |
| 5,181,234 A | 1/1993 | Smith | |
| 5,182,764 A | 1/1993 | Peschmann et al. | |
| 5,221,843 A | 6/1993 | Alvarez | |
| 5,224,144 A | 6/1993 | Annis | |
| 5,237,598 A | 8/1993 | Albert | |
| 5,247,561 A | 9/1993 | Kotowski | |
| 5,253,283 A | 10/1993 | Annis et al. | |
| 5,313,511 A | 5/1994 | Annis et al. | |
| 5,367,552 A | 11/1994 | Peschmann | |
| 5,379,334 A | 1/1995 | Zimmer et al. | |
| 5,493,596 A | 2/1996 | Annis | |
| 5,548,123 A | 8/1996 | Perez-Mendez et al. | |
| 5,600,303 A * | 2/1997 | Husseiny et al. | 378/57 |
| 5,638,420 A | 6/1997 | Armistead | |
| 5,642,393 A | 6/1997 | Krug et al. | |
| 5,642,394 A | 6/1997 | Rothschild | |
| 5,666,393 A | 9/1997 | Annis | |
| 5,687,210 A | 11/1997 | Maitrejean et al. | |
| 5,692,028 A | 11/1997 | Geus et al. | |
| 5,751,837 A | 5/1998 | Watanabe et al. | |
| 5,764,683 A | 6/1998 | Swift et al. | |
| 5,768,334 A | 6/1998 | Maitrejean et al. | |
| 5,787,145 A | 7/1998 | Geus | |
| 5,805,660 A | 9/1998 | Perion et al. | |
| 5,838,759 A | 11/1998 | Armistead | |
| 5,903,623 A | 5/1999 | Swift et al. | |
| 5,910,973 A | 6/1999 | Grodzins | |
| 5,930,326 A | 7/1999 | Rothschild et al. | |
| 5,940,468 A | 8/1999 | Huang et al. | |
| 5,974,111 A | 10/1999 | Krug et al. | |
| 6,031,890 A | 2/2000 | Bermbach et al. | |
| 6,058,158 A | 5/2000 | Eiler | |
| 6,067,344 A | 5/2000 | Grodzins et al. | |
| 6,081,580 A | 6/2000 | Grodzins et al. | |
| 6,094,472 A | 7/2000 | Smith | |
| 6,151,381 A | 11/2000 | Grodzins et al. | |
| 6,188,747 B1 | 2/2001 | Geus et al. | |
| 6,192,101 B1 | 2/2001 | Grodzins | |
| 6,192,104 B1 | 2/2001 | Adams | |
| 6,195,413 B1 | 2/2001 | Geus et al. | |
| 6,198,795 B1 | 3/2001 | Naumann et al. | |
| 6,218,943 B1 | 4/2001 | Ellenbogen | |
| 6,249,567 B1 | 6/2001 | Rothschild et al. | |
| 6,252,929 B1 | 6/2001 | Swift et al. | |
| 6,256,369 B1 | 7/2001 | Lai | |
| 6,278,115 B1 | 8/2001 | Annis et al. | |
| 6,282,260 B1 | 8/2001 | Grodzins | |
| 6,292,533 B1 | 9/2001 | Swift et al. | |
| 6,301,326 B2 | 10/2001 | Bjorkholm | |
| 6,320,933 B1 | 11/2001 | Grodzins et al. | |
| 6,347,132 B1 | 2/2002 | Annis | |
| 6,356,620 B1 | 3/2002 | Rothschild et al. | |
| 6,424,695 B1 | 7/2002 | Grodzins et al. | |
| 6,434,219 B1 | 8/2002 | Rothschild et al. | |
| 6,435,715 B1 | 8/2002 | Betz et al. | |
| 6,442,233 B1 | 8/2002 | Grodzins et al. | |
| 6,445,765 B1 | 9/2002 | Frank et al. | |
| 6,453,003 B1 | 9/2002 | Springer et al. | |
| 6,453,007 B2 | 9/2002 | Adams et al. | |
| 6,456,684 B1 | 9/2002 | Mun et al. | |
| 6,459,761 B1 | 10/2002 | Grodzins et al. | |
| 6,459,764 B1 | 10/2002 | Chalmers et al. | |
| 6,473,487 B1 | 10/2002 | Le | |
| RE37,899 E | 11/2002 | Grodzins et al. | |
| 6,483,894 B2 | 11/2002 | Hartick et al. | |
| 6,507,025 B1 | 1/2003 | Verbinski et al. | |
| 6,532,276 B1 | 3/2003 | Hartick et al. | |
| 6,542,574 B2 | 4/2003 | Grodzins | |
| 6,542,578 B2 | 4/2003 | Ries et al. | |
| 6,542,580 B1 | 4/2003 | Carver et al. | |
| 6,546,072 B1 * | 4/2003 | Chalmers | 378/57 |
| 6,552,346 B2 | 4/2003 | Verbinski et al. | |
| 6,563,903 B2 | 5/2003 | Kang et al. | |
| 6,580,778 B2 | 6/2003 | Meder | |
| 6,584,170 B2 | 6/2003 | Aust et al. | |
| 6,597,760 B2 | 7/2003 | Beneke et al. | |
| 6,606,516 B2 | 8/2003 | Levine | |
| 6,636,581 B2 | 10/2003 | Sorenson | |
| 6,653,588 B1 | 11/2003 | Gillard-Hickman | |
| 6,658,087 B2 | 12/2003 | Chalmers et al. | |
| 6,663,280 B2 | 12/2003 | Doenges | |
| 6,665,373 B1 | 12/2003 | Kotowski et al. | |
| 6,665,433 B2 | 12/2003 | Roder | |
| 6,735,279 B1 * | 5/2004 | Jacobs et al. | 378/86 |
| 6,763,635 B1 | 7/2004 | Lowman | |
| 6,785,357 B2 | 8/2004 | Bernardi et al. | |
| 6,812,426 B1 | 11/2004 | Kotowski et al. | |
| 6,816,571 B2 | 11/2004 | Bijjani et al. | |
| 6,837,422 B1 | 1/2005 | Meder | |
| 6,839,403 B1 | 1/2005 | Kotowski et al. | |
| 6,843,599 B2 | 1/2005 | Le et al. | |
| 6,920,197 B2 | 7/2005 | Kang et al. | |
| 7,039,159 B2 | 5/2006 | Muenchau et al. | |
| 7,166,844 B1 | 1/2007 | Gormley et al. | |
| 7,207,713 B2 | 4/2007 | Lowman | |
| 7,609,807 B2 * | 10/2009 | Leue et al. | 378/57 |
| 2004/0017888 A1 * | 1/2004 | Seppi et al. | 378/57 |
| 2004/0086078 A1 | 5/2004 | Adams et al. | |
| 2004/0125914 A1 | 7/2004 | Kang et al. | |
| 2004/0141584 A1 | 7/2004 | Bernardi et al. | |
| 2004/0258198 A1 | 12/2004 | Carver et al. | |
| 2005/0117700 A1 | 6/2005 | Peschmann | |
| 2005/0135668 A1 | 6/2005 | Polichar et al. | |
| 2005/0156734 A1 | 7/2005 | Zerwekh et al. | |
| 2005/0157842 A1 | 7/2005 | Agrawal et al. | |
| 2005/0169421 A1 | 8/2005 | Muenchau et al. | |
| 2006/0284094 A1 | 12/2006 | Inbar | |
| 2007/0110215 A1 | 5/2007 | Hu et al. | |
| 2007/0140423 A1 | 6/2007 | Foland | |
| 2007/0172129 A1 | 7/2007 | Tortora | |
| 2007/0189454 A1 | 8/2007 | Georgeson et al. | |
| 2007/0210255 A1 | 9/2007 | Bjorkholm | |
| 2007/0269005 A1 | 11/2007 | Chalmers et al. | |
| 2007/0280416 A1 | 12/2007 | Bendahan et al. | |
| 2007/0280502 A1 | 12/2007 | Paresi et al. | |
| 2007/0286337 A1 | 12/2007 | Wang et al. | |
| 2008/0044801 A1 | 2/2008 | Modica et al. | |
| 2008/0304622 A1 | 12/2008 | Morton | |

FOREIGN PATENT DOCUMENTS

| | | |
|---|---|---|
| EP | 0176314 | 4/1986 |
| EP | 0919186 | 6/1999 |
| EP | 1413898 | 4/2004 |
| GB | 2255634 | 11/1992 |
| WO | WO 9855851 | 10/1998 |

(56) References Cited

FOREIGN PATENT DOCUMENTS

| WO | WO 2004010127 | 1/2004 |
|---|---|---|
| WO | WO 2005098400 | 10/2005 |
| WO | WO 2006/036076 | 4/2006 |
| WO | WO 2006/045019 | 4/2006 |
| WO | WO 2006/078691 | 7/2006 |
| WO | WO 2007/051092 | 5/2007 |
| WO | WO 2008/017983 | 2/2008 |

OTHER PUBLICATIONS

Search Report PCT/GB2009/000497, Jan. 26, 2010, Rapiscan Security Products, Inc.

International Search Report PCT/GB2009/001444, Dec. 17, 2009, Rapiscan Security Products.

Search Report for WO2009/106847, Sep. 3, 2009, Rapiscan Security Products.

International Seacrh Report PCT/GB2009/001277, May 20, 2008, Rapiscan Systems, Inc.

International Search Report PCT/GB2009/001275, Nov. 26, 2009, Rapiscan Security Products, Inc.

"Mobile X-Ray Inspection Systems", Internet Citation, Feb. 12, 2007, pp. 1-2, URL:http://web.archive.org/web/20070212000928/http://www.bombdetection.com/cat_details.php?catid=20>.

Molchanov et al., "Nanosecond Gated Optical Sensors for Ocean Optic Applications," Sensors Applications Symposium, 2006, Proceedings of the 2006 IEEE, Feb. 7, 2006, 147-150.

* cited by examiner

US 8,831,176 B2

HIGH ENERGY X-RAY INSPECTION SYSTEM USING A FAN-SHAPED BEAM AND COLLIMATED BACKSCATTER DETECTORS

CROSS-REFERENCE TO RELATED APPLICATIONS

The present application is a national stage application of PCT/GB2009/001275, filed on May 20, 2009, which relies on Great Britain Patent Application Number 0809107.6, filed on May 20, 2008.

FIELD OF THE INVENTION

The present application relates to scanning systems. It has particular application in scanning systems for cargo, but can also be used in scanners for other applications such as security and high energy medical scanners. There exists a requirement for screening of cargo items for the detection of illicit materials and devices.

BACKGROUND

Increasingly frequently, scanning systems involve the use of high energy inspection equipment based on transmission imaging with X-radiation generated by an X-ray linear accelerator with typical beam quality of 1 MeV to 9 MeV.

Such systems are very effective at probing the structure and shape of relatively high atomic number articles but are less effective at locating the presence of low atomic number materials in sheet like configurations that are broadly perpendicular to the path of the incoming X-ray beam.

FIG. 1 is a schematic representation of a known system 2. The known system 2 comprises an x-ray source, in the form of a rotating disc x-ray source 4. An object to be scanned is shown in the form of a lorry 8. A detector 6 is arranged on the same side of the lorry as the source. The source is arranged to irradiate a single region of the object at any one time (i.e. in any one irradiation event or burst). The source produces a tightly collimated beam 10 which irradiates a point on the object 8. Scattered radiation 12 is scattered in all directions and is detected at the detector 6. The detector 6 measures the amount of radiation per irradiation event in order to provide information on the point of the object being irradiated during that event.

The inverse square law indicates that the intensity of a radiation beam reduces in proportion to the square of the distance from the source. For example, the source intensity (photons/unit area) drops by a factor of four in moving from 10 cm away from a point source of radiation to the same area 20 cm away. Therefore, the strength of the backscatter signal drops rapidly with distance into the cargo and so X-ray backscatter is predominantly a surface inspection technique.

Further, it can easily be shown that the maximum energy of a backscattered X-ray photon is 256 keV. This relatively low energy X-ray is absorbed rather readily by high density materials such as steel, again suggesting that X-ray backscatter imaging is predominantly a surface imaging method.

Therefore, what is needed is an X-ray backscatter imaging that is integrated with high intensity linear accelerator based transmission imaging in order to spatially correlate surface X-ray backscatter imaging with bulk object transmission imaging as a further investigation in detection of illicit materials and objects in cargo items.

SUMMARY OF THE INVENTION

In some embodiments of the present invention, it is recognised that there is advantage in combining X-ray backscatter imaging with high intensity linear accelerator based transmission imaging in order to spatially correlate surface X-ray backscatter imaging with bulk object transmission imaging as a further investigation in detection of illicit materials and objects in cargo items.

In one embodiment, the present invention provides a scanning system for scanning an object in a scanning zone. The system comprises a radiation source arranged to irradiate the object with radiation having a peak energy of at least 900 keV. The system also comprises a scatter detector arranged to detect radiation scattered from the object wherein the radiation source is arranged to irradiate the object over a plurality of regions to be scanned within a single irradiation event. The scatter detector comprises a plurality of detection elements, each detection element being arranged to detect scattered radiation from a predefined part of the scanning zone and a signal processor arranged to calculate scatter intensity across the plurality of detector elements.

BRIEF DESCRIPTION OF THE DRAWINGS

Embodiments of the invention will now be described, by way of example only, with reference to the accompanying drawings in which.

DETAILED DESCRIPTION OF THE DRAWINGS

The present invention is directed towards combining X-ray backscatter imaging with high intensity linear accelerator based transmission imaging in order to spatially correlate surface X-ray backscatter imaging with bulk object transmission imaging as a further investigation in detection of illicit materials and objects in cargo items.

In this situation, X-ray backscatter imaging can be a useful addition to the diagnostic arsenal. Known systems tend to utilise a tightly collimated radiation beam that is scanned mechanically across the region of interest with a large area detector positioned to capture as many as possible of the backscattered X-ray photons. An image can be formed by correlating the count rate from the detector with the known point of intersection of the X-ray beam with the item under inspection.

The independent claims define aspects of the invention for which protection is sought. The dependent claims define preferable inventive features. Any of the features of the dependent claims may be used in combination with the features of other claims, even if they are not explicitly dependent upon them— this will be clear to a person skilled in this field. Where a feature is claimed in one category (e.g. method, system, detector arrangement, etc.) protection is sought for that feature in other categories even if not explicitly claimed.

Figure 1:
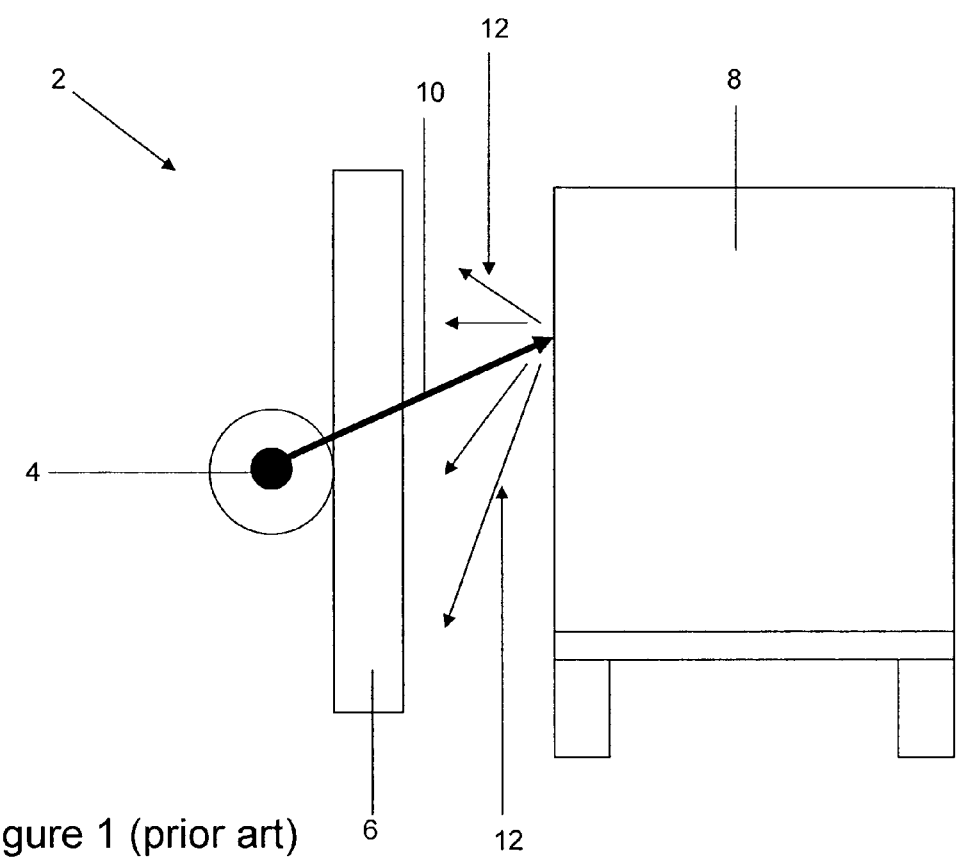
FIG. 1 schematically shows a prior art scanning system.
Figure 2:
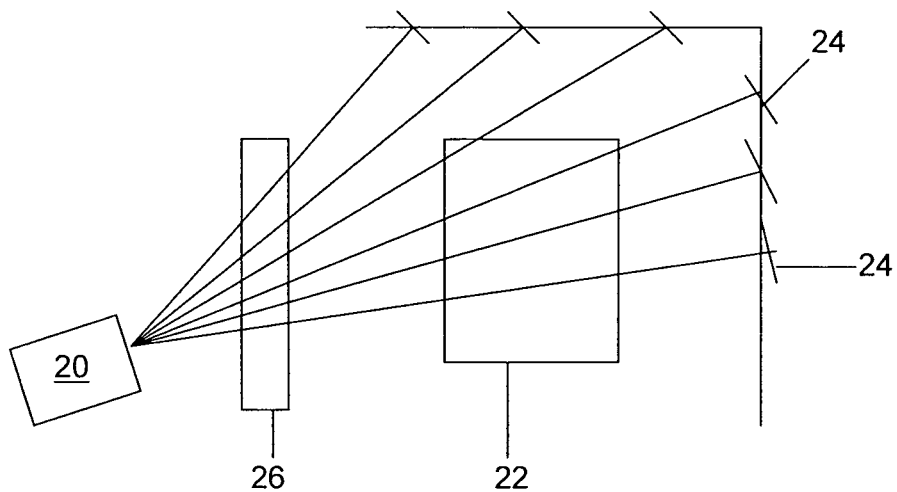
FIGS. 2 to 4 schematically show parts of a scanning system according to an embodiment of this invention.
Figure 3:
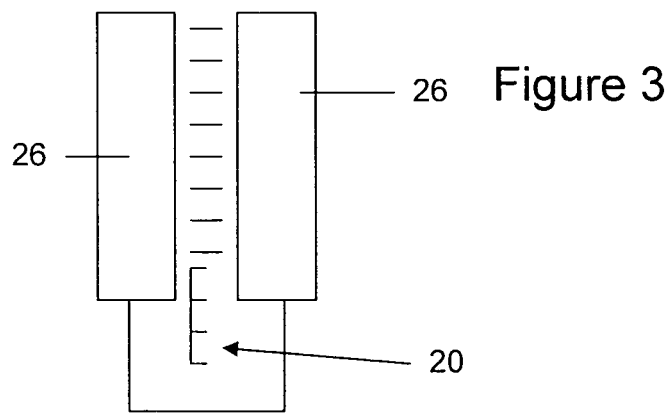
Figure 4:
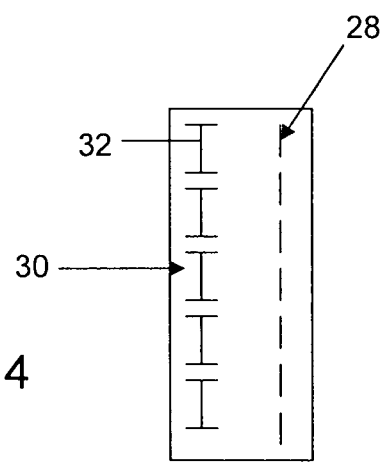

A system configuration according to an embodiment of the invention is outlined in FIGS. 2 to 4. Here, an X-ray linear accelerator 20 is used to fire a collimated fan-beam of high energy (at least 900 keV) X-radiation through an object 22 under inspection and so to a set of X-ray detectors 24 which can be used to form a high resolution transmission X-ray imaging of the item under inspection. The X-ray linear accelerator beam is pulsed, so that as the object under inspection moves through the beam, the set of one-dimensional projections can be acquired and subsequently stacked together to form a two-dimensional image.

In this embodiment, an X-ray backscatter detector 26 is placed close to the edge of the inspection region on the same side as the X-ray linear accelerator 20 but offset to one side of the X-ray beam so that it does not attenuate the transmission X-ray beam itself. As shown in FIG. 3, it is advantageous to use two backscatter imaging detectors 26, one on either side of the primary beam. In some embodiments the backscatter detectors may be arranged differently. In some embodiments there may be only one backscatter detector. In other embodiments there may be more than two such detectors.

In contrast to known backscatter imaging detectors which use the localisation of the incident X-ray beam to define the scattering region, the backscatter imaging detector described here is able to spatially correlate the intensity of backscattered X-ray signals with their point of origin regardless of the extended fan-beam shape of the X-ray beam.

In the backscatter imaging detector 26 of this embodiment, this spatial mapping is performed using a segmented collimator 28 in zone plate configuration as shown schematically in FIG. 4. Normally, a zone plate will comprise a series of sharply defined patterns whose impulse response function is well known in the plane of a two-dimensional imaging sensor that is located behind the sensor. In the present case, the energy of the X-ray beam to be detected is typically in the range 10 keV to 250 keV and so the edges of the zone plate pattern will not be sharp. For example, a zone plate fabricated using lead will require material of thickness typically 2 mm to 5 mm. Further, it is expensive to fabricate a high resolution two-dimensional imaging sensor of the size that is required in this application.

Figure 5:
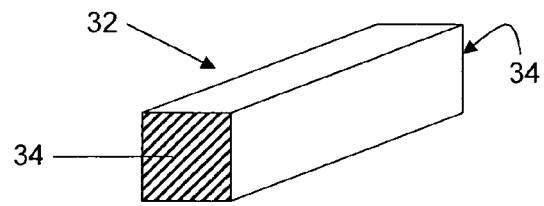
FIG. 5 schematically shows a detector element according to an embodiment of this invention.

However, it is noted that the radiation beam is well collimated in one direction (the width of the radiation fan beam) and therefore the imaging problem is reduced to a one-dimensional rather than a two-dimensional problem. Therefore a backscatter detector in the form of an effectively one dimensional imaging sensor 30 is provided behind the zone plate 28. To address this problem an elemental backscatter detector is used in this embodiment. As shown in FIG. 4, the detector 30 comprises a plurality of detector elements 32. FIG. 5 illustrates a detector element 32 suitable for use in this example. Here, the detector element 32 comprises a bar of scintillation material (about 100 mm long in this example) and is supplied with a photo-detector 34 at either end. The photo-detector 34 may advantageously be a semiconductor photodiode or a photomultiplier tube. X-ray photons that interact in the scintillation material emit light photons and these will travel to the two photo-detectors where they may be detected. It may be shown that the intensity of the light reaching each photo-detector is in proportion to the distance of the point of interaction from the face of the photo-detector. Therefore, by measuring the relative intensity at the two photo detectors, the point of interaction of the X-ray photon with the detector can be resolved.

Figure 6:
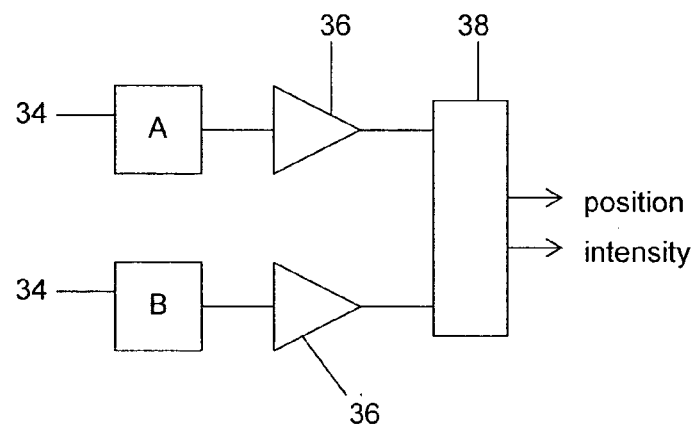
FIG. 6 illustrates a circuit for converting the detector element output position-sensitive according to an embodiment of this invention.

A suitable circuit for resolving the position of interaction is shown in FIG. 6. Here each photo detector 34 is connected to its own amplifier 36 whose analogue output is fed into a position logic block 38. In this block, the magnitude of the output from each detector is digitised and the resulting digital values are ratioed in order to find the point of interaction. The sum of the two outputs gives the total energy deposited in the detector during the interaction.

Figure 8:
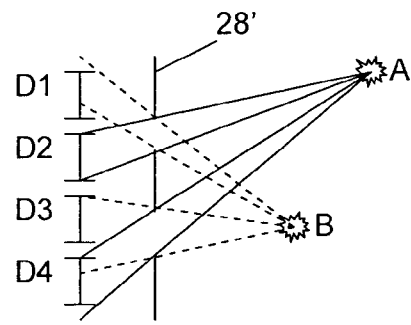
FIG. 8 graphically illustrates the effect of a type of zone plate on backscatter radiation distribution.

The basic principle of operation of a zone plate 28' is described in FIG. 8. Consider a radiation source at point A. Radiation from this source will pass through apertures in the zone plate resulting in exposure of the detectors. The masking effect of the zone plate 28' is to cause exposure of detectors D2 and D4 in this example with no exposure of detectors D1 and D3. However, radiation from source point B results in exposure to detectors D1 and D3 with no exposure of detector D2 and little exposure on detector D4. An algorithm can therefore be determined that analyses the pattern of detector exposures to allocate each measured pattern with a particular radiation source position.

In the chosen embodiment, things are a bit more complex since the X-ray linear accelerator is a pulsed source with a pulse width of typically 5 μs and a dead time between pulses of typically 10 ms. Therefore, scatter data for all points in the object under inspection will be received simultaneously and standard analysis of the detector data will not yield a reasonable result.

Figure 9:
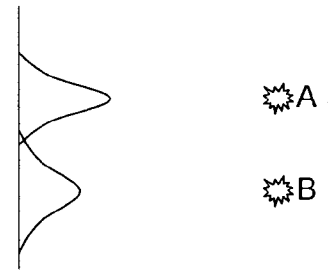
FIG. 9 graphically illustrates the effect of a type of zone plate on backscatter radiation distribution.

In the present invention, it is recognised that, due to the inverse square law, the intensity of the backscattered signal at the detector is to first order matched by the distribution of scattering objects immediately opposite to the detector. This is illustrated in FIG. 9. Therefore, a position resolving detector can to first order determine the scatter profile from the object under inspection even in the absence of any collimation. The closer the scattering object is to the detector, the sharper the spatial resolution of the data and the higher the count rate at the detector.

Figure 10:
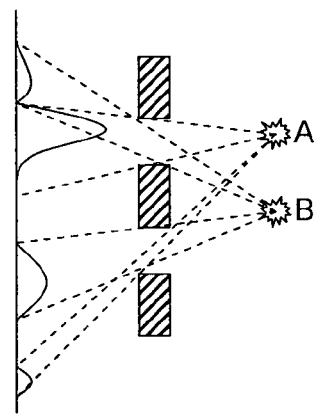
FIG. 10 graphically illustrates the effect of a type of zone plate on backscatter radiation distribution.

If a coarse collimator is then added as shown in FIG. 10, further information can be determined to sharpen up the scatter signal, but at the expense of overall detected signal. In this stylised diagram, the signal from source point A is now better defined, but the signal from source point B is all but attenuated away by the collimator. In practice, there is a trade-off between detection efficiency and image resolution and this is affected by practical issues such as acceptable dose levels, cost and complexity.

Figure 7:
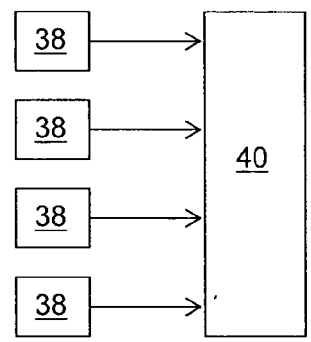
FIG. 7 illustrates a circuit for calculating scatter intensity across the detector elements.

In this embodiment however, a data acquisition system is required of the form shown in FIG. 7 where data from each detector element (generally in the form of position and intensity) is interpreted by a signal processor 40 in order to calculate a one-dimensional scatter intensity distribution along the length of the fan-beam of X-rays that passes through the object under inspection.

In a further aspect of this invention, transmission X-ray data that is collected simultaneously with the scatter information can be used to constrain the activity of the signal processor shown in FIG. 7 by providing a-priori information as to the location and extent of objects that may constitute a scattering object. This high quality spatial information can be used to prepare the scatter image data for operator review on a workstation screen, for example.

Figure 11:
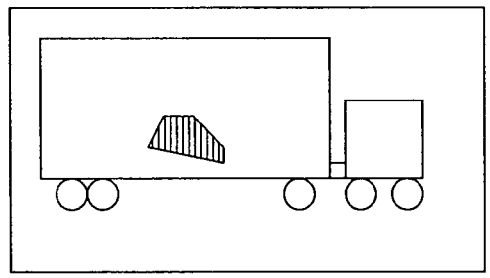
FIG. 11 is a representation of a display output according to the invention and visible by an operator of the scanning system.

A base level of X-ray scattering will be observed across the whole image and this information is both anticipated and uninteresting. What is of relevance to the operator is to resolve significant changes in the X-ray backscatter signal that may denote the presence of an illicit material or device. Therefore, in a further aspect of this invention, the signal processor can be used to subtract a base-line offset from all X-ray backscatter signals such that the remaining data contains only significant scatter signal. The signal processor should include the ability to filter the X-ray backscatter signals to ensure that only significant information is passed onto the operator workstation screen as shown overlaid on the transmission X-ray image in FIG. 11.

A suitable statistically driven noise filtering algorithm will take the mean and variance in the backscatter signal from all detector elements and compare these against background levels. When a statistically significant difference is seen between the signal at a given detector and that in the background, the signal is passed through to the output otherwise the signal is set to zero. A statistically significant difference is one where the detected signal is greater than a constant multiple of the background standard deviation. A suitable constant would be one standard deviation above background.

In another embodiment of this invention, the signal processor will provide two-dimensional statistical filtering of the X-ray backscatter signal with a dilate-erode based image segmentation algorithm to clearly localise and define the X-ray backscatter region.

The displayed X-ray backscatter image will advantageously be colour coded in order to provide an indication of the intensity of backscatter data which is loosely related to the density of the scattering object. The data must first be normalised to reflect the varying distance between the X-ray source and the edge of the scattering cargo item under inspection.

In some embodiments the object is irradiated with higher energy radiation, e.g. 1 MeV, 2 MeV, 3 MeV or higher etc.

In some embodiments different types of zone plates may be used—the skilled person will be able to ascertain form the teaching of this document suitable zone plate configuration.

Different detector elements may be used—for example different position sensitive detector elements.

I claim:

1. A scanning system for scanning an object in a scanning zone, the system comprising
   an X-ray radiation source arranged to irradiate the object with X-ray radiation having a peak energy of at least 900 keV and having a beam collimated in one direction;
   a scatter detector arranged to detect X-ray radiation scattered from the object wherein the X-ray radiation source is arranged to irradiate the object over a plurality of regions to be scanned within a single irradiation event, the scatter detector comprising
      a plurality of detection elements, each detection element being a one dimensional imaging sensor arranged into detector regions, each detector region arranged to detect scattered X-ray radiation from a corresponding part of the scanning zone;
      a mask arranged to restrict scattered radiation not from the corresponding part of the scanning zone from reaching its corresponding detector region, wherein said mask is configured to create an exposure pattern across multiple detection elements; and
   a signal processor arranged to calculate scatter intensity across the plurality of detector elements and analyze said exposure pattern to determine a particular radiation source position.

2. The system of claim 1 wherein the plurality of regions are adjacent to each other.

3. The system of claim 2 wherein the plurality of regions are linearly arranged.

4. The system of claim 1 comprising movement means arranged to provide relative movement between the object and the X-ray radiation source such that a different plurality of regions is scanned with a different irradiation event.

5. The system of claim 4 wherein the movement means is arranged to provide movement such that a different plurality of regions is scanned with each different irradiation event.

6. The system of claim 4 wherein the different pluralities of regions cover substantially the whole object or substantially all of the areas of interest on the object.

7. The system of claim 1 wherein the X-ray radiation source is arranged to irradiate the object in discrete bursts and a single irradiation event comprises one of the discrete bursts.

8. The system of claim 1 wherein the scatter detector is arranged to detect X-ray radiation from a plurality of regions to be scanned substantially simultaneously.

9. The system of claim 1 wherein the scatter detector is arranged to detect X-ray radiation from the plurality of regions in response to the X-ray radiation source which is arranged to irradiate the object in discrete bursts.

10. The system of claim 1 wherein a detector region and its corresponding part of the scanning zone are arranged such that the distance between them is minimized.

11. The system of claim 1 wherein each detector element comprises a position sensitive detector element.

12. The system of claim 11 wherein the position sensitive detector or each position sensitive detector element comprises a scintillation crystal.

13. The system of claim 1 wherein the mask comprises a plate arranged to restrict scattered X-ray radiation from passing through it, the plate having apertures therethrough, the apertures being arranged to allow scattered X-ray radiation to pass through the mask.

14. The system of claim 13 wherein the apertures are arranged to correspond in position to the parts of the scanning zone such that each aperture is as close as possible to its corresponding part of the scanning zone.

15. The system of claim 1 wherein the scatter detector comprises a backscatter detector arranged on the same side of the object as the source.

16. The system of claim 1 further comprising a transmission detector arranged to detect X-ray radiation which passes through the object and a controller arranged to receive and process information from the transmission detector in order to identify regions of the object of particular interest.

17. The system of claim 16 wherein the controller is arranged to superimpose the information received from the transmission detector upon information received from the scatter detector.

18. The system of claim 17 comprising imaging means arranged to generate an image of the object and of any regions of particular interest, wherein the controller is arranged to instruct the imaging means to create the image using superimposed information such that scatter detector information is at least partially constrained outside regions that have been identified as regions of particular interest based upon the transmission detector information.

19. The system of claim 16 wherein the controller is arranged to control operation of the scatter detector based upon the identified regions of particular interest.

* * * * *